(12) United States Patent
Chalana et al.

(10) Patent No.: US 7,004,904 B2
(45) Date of Patent: *Feb. 28, 2006

(54) IMAGE ENHANCEMENT AND SEGMENTATION OF STRUCTURES IN 3D ULTRASOUND IMAGES FOR VOLUME MEASUREMENTS

(75) Inventors: Vikram Chalana, Mill Creek, WA (US); Stephen Dudycha, Bothell, WA (US); Gerald McMorrow, Kirkland, WA (US)

(73) Assignee: Diagnostic Ultrasound Corporation, Bothell, WA (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/633,186

(22) Filed: Jul. 31, 2003

(65) Prior Publication Data

US 2004/0024315 A1    Feb. 5, 2004

Related U.S. Application Data

(63) Continuation-in-part of application No. 10/443,126, filed on May 20, 2003.

(60) Provisional application No. 60/470,525, filed on May 12, 2003, provisional application No. 60/423,881, filed on Nov. 5, 2002, provisional application No. 60/400,624, filed on Aug. 2, 2002.

(51) Int. Cl.
*A61B 8/00* (2006.01)

(52) U.S. Cl. ............. 600/443; 600/446; 600/449
(58) Field of Classification Search ........ 600/437–472; 73/625, 626; 367/7, 11, 130; 128/916; 382/181
See application file for complete search history.

(56) References Cited

U.S. PATENT DOCUMENTS

| 5,235,985 A | 8/1993 | McMorrow et al. |
| 5,588,435 A | 12/1996 | Weng et al. |
| 5,605,155 A | 2/1997 | Chalana et al. |

(Continued)

OTHER PUBLICATIONS

Sagiv C., et al., "Application of a Semiautomatic Boundary Detection Algorithm for the Assessment of Amniotic Fluid Quantity from Ultrasound Images," Ultrasound in Medicine & Biology, 1999, vol. 25, No. 4, pp. 515-526.

(Continued)

*Primary Examiner*—Ali Imam
(74) *Attorney, Agent, or Firm*—Richard T. Black; Black Lowe & Graham PLLC (57) ABSTRACT

A segmentation algorithm is optimized to robustly locate and measure the volume of fluid filled or non-fluid filled structures or organs from imaging systems derived from ultrasound, computer assisted tomography, magnetic resonance, and position emission tomography. A clinical specimen is measured with a plurality of 2D scan planes processed by the segmentation algorithm to estimate the 2D based area the 3D based volumes of fluid-filled and non-fluid filled organs or structures.

27 Claims, 9 Drawing Sheets

U.S. PATENT DOCUMENTS

| | | |
|---|---|---|
| 5,644,513 A | 7/1997 | Rudin et al. |
| 6,213,949 B1 | 4/2001 | Ganguly et al. |
| 6,346,124 B1 | 2/2002 | Geiser et al. |
| 6,375,616 B1 | 4/2002 | Soferman et al. |
| 6,695,780 B1 | 2/2004 | Nahum et al. |
| 2002/0133075 A1 | 9/2002 | Abdelhak |

OTHER PUBLICATIONS

E.F. Magann et al., Ultrasound estimation of Amniotic Fluid Volume Using the Largest Vertical Pocket Containing Umbilical Cord: Measure to or Through the Cord?, Ultrasound Obstet Gynecol 2002; 20: 464-467.

Gramellini et al., Sonographic Assessment of Amniotic Fluid Volume Between 11 and 24 Weeks of Gestation: Construction of Reference intervals Related to Gestational Age, Ultrasound Obstet Gynecol 2001: 17: 410-415.

Mann et al., Novel Technique for Assessing Amniotic Fluid Volume Use of a Three-Dimensional Bladder Scanner, The Journal of Maternal-Fetal Medicine 9:308-310 (2000)

Grover et al., Three-Dimensional Method for Determination of Amniotic Fluid Volume in Intrauterine Pockets, Obstetrics and Gynecology 1997; 90, No. 6: 1007-1010.

Cheng et al., Boundary Extraction Method for Three Dimensional Ultrasonic Echo Imaging Using Fuzzy and Relaxation Techniques, TNE 1993 IEEE, Nuclear Science Symposium: Medical Imaging Oct. 30-Nov. 6, 1993: PT 3, 1610-1614.

Ross, Michael G., Am J. Obstet Gynecol Aug. 1993: vol. 169, No. 2: 435-437.

FIG. 5B Heat and shock filtering of blurred noisy signal
— original signal
-- noisy signal
····· cleaned by heat flow
▪▪▪ shock filtered heat flow

IMAGE ENHANCEMENT AND SEGMENTATION OF STRUCTURES IN 3D ULTRASOUND IMAGES FOR VOLUME MEASUREMENTS

PRIORITY CLAIM

This application is a continuation-in-part of and claims priority to U.S. patent application Ser. No. 10/443,126 filed May 20, 2003 which claims priority to U.S. provisional patent application Ser. No. 60/423,881 filed Nov. 5, 2002 and to U.S. provisional application 60/400,624 filed Aug. 2, 2002. This application claims priority to U.S. provisional patent application Ser. No. 60/470,525 filed May 12, 2003, and to U.S. patent application Ser. No. 10/165,556 filed Jun. 7, 2002, now U.S. Pat. No. 6,676,605. All of the above applications are herein incorporated by reference in their entirety as if fully set forth herein.

FIELD OF THE INVENTION

This invention pertains to the field of medical imaging, particularly to measuring the size and shape of organs from three-dimensional images.

BACKGROUND OF THE INVENTION

Various kinds of methods have been used or proposed in the literature to measure the size, shape, and internal volumes of specific organs using ultrasound segmentation analysis from three-dimensional ultrasound images. Examples of body structures undergoing segmentation analysis include heart chambers, particularly cardiac chambers (left and right ventricles, left and right atriums, the prostate, the bladder, and amniotic sacs.

The measurement of heart chambers is described, for example in U.S. Pat. No. 6,346,124 to Geiser, et al. (Autonomous Boundary Detection System For Echocardiographic Images). Similarly, the measurement of bladder structures are covered in U.S. Pat. No. 6,213,949 to Ganguly, et al. (System For Estimating Bladder Volume) and U.S. Pat. No. to 5,235,985 to McMorrow, et al., (Automatic Bladder Scanning Apparatus). The measurement of fetal head structures is described in U.S. Pat. No. 5,605,155 to Chalana, et al., (Ultrasound System For Automatically Measuring Fetal Head Size). The measurement of fetal weight is described in U.S. Pat. No. 6,375,616 to Soferman, et al. (Automatic Fetal Weight Determination).

Most of these techniques are not ideal in that they cannot be generalized beyond the application for which they were designed. They use shape or size assumptions that are not necessarily satisfied for different applications. An attempt to make a generalized model is described in U.S. Pat. No. 5,588,435 to Weng, et al. (System And Method For Automatic Measurement Of Body Structures) but is limited in its application due to method complexity and operational robustness.

The techniques commonly employed in segmentation use active contour modeling and live wire methods to delineate an object shape within electronic-based images, and partial differential equation (PDE) based processing of image signals to reduce background noise speckle. These three methods have their advantages and disadvantages. For example, the active contour modeling method or "snakes" is a region-based boundary method and requires specific shape assumptions and the use of deformable models to work properly (M. Kass, A. Witkin, D. Terzopolous, "Snakes: Active Contour Models," International Journal of Computer Vision, pp. 321–331, 1988). However, "snake" methods require an initial contour that needs to be very close to the final desired boundary. In addition, most of these methods are iterative in nature and labor intensive.

Live wire methods, championed by A. X. Falacao et al. in "User-steered Image Segmentation Paradigms: Live wire and Live Lane," (A. X. Falacao, J. K. Udupa, S. Samarasekara, and S. Sharma, Graphical Models and Image Processing, 60, 233–26-, 1998) and E. W. Dijkstra, in "A note on two problems in connection with graphs," (Numerical Math, vol. 1, pp. 269–271, 1959), requires a user to actively provide a starting point and an ending point via a mouse, pointer, or equivalent delineation means. Live wire is an interactive segmentation method which uses a minimum cost path between the last clicked user point to the current mouse clicked location. The live wire methodology of Falacao is labor intensive since it requires an iterative approach and generates a series of mouse delineating endpoints. Furthermore, live wire methods are limited in accuracy because the simplest optimal path contour connecting any two mouse determined end-points is not sufficient in ultrasound images that are prone to mouse pointer backtracking. That is, the "user-steering" methods of Falacao require that the user backtrack the mouse whenever the drawn contour line has lost track of the object boundary as presented on the ultrasound image.

Most ultrasound processing methods involve some preprocessing techniques to reduce speckle noise and enhance images, such as median filtering methods and PDE-based image processing. PDE-based methods have the added advantages of preserving edges while enhancing images (see P. Perona and J. Malik, "Scale-space and edge detection using aniostropic diffusion," IEEE Trans. Pattern Analysis and Machine Intelligence, vol. 12, July 1990, pp. 629–639; J. A. Sethian, Level Set Methods and Fast Marching Methods, 2nd Edition, Cambridge University Press, 1999; S. Osher and L. I. Rudin, "Feature-oriented image enhancement using shock filters," SIAM Journal of Numerical Analysis, vol. 27, pp. 919–940, August 1990; and U.S. Pat. No. 5,644,513 to Rudin, et al. "System Incorporating Feature-Oriented Signal Enhancement Using Shock Filters"). These methods, especially shock filters for image sharpening or blind deconvolution, have been used reducing noise speckle for computerized-tomography (CT), magnetic resonance (MR), and positron emission-tomography (PET) images. However, shock filters implemented with unoptimized algorithms have been found deficient in that the unoptimized algorithms increase or enhance noise speckle, thereby degrading the CT, MR, and PET images.

In ultrasound images, chamber-like structures (for example: bladder, heart left ventricle, prostate, amniotic sac) are further prone to image degradation due to ultrasound echoes reflecting from other surfaces parallel to do organ wall boundary. The echoes from the parallel surfaces present as bright regions overlapping with the dark chamber boundary walls. Thus, ultrasound-echoing overlaps creates missing lateral boundaries of the organ walls. Thereby, making it difficult to accurately determine boundary wall locations where segmentation lines need to be drawn.

Thus, there is a need for a generalized image analysis method to accurately measure the size, shape, and volumes of fluid-filled and non-fluid filled organs from analysis of one-dimensional (1D), two-dimensional (2D), and three-dimensional (3D) images from ultrasound, CT, MR, and PET procedures. The generalized image analysis method requires optimal algorithms to minimize background noise speckle and maximize structure segmentation or delineation by minimizing the creation of missed lateral boundaries of organ structures. The generalized image analysis method needs to be broadly adaptable and simple to implement.

SUMMARY OF THE INVENTION

The invention is a method having a plurality of segmentation algorithms and steps optimized to robustly locate and measure the volume of a fluid filled or non-fluid filled structure or organ from primary images obtained from instruments probing with or receiving and processing electromagnetic and non-electromagnetic radiation including ultrasound, CT, MR, PET, and radioisotopes used in nuclear medicine procedures that produce a plurality of, 1D, 2D, or 3D images. The method is applied to 1D scans to obtain resultant 2D primary images. Each 2D primary image is made visually enhanced by the plurality of segmentation algorithms and steps of the method. The method then includes the creation and placement of accurately drawn boundary line contours that more clearly delineate or segment the structure walls within the 2D image. Upon placing the boundary line contours, the method calculates the volumes for each delineated structure or organ presented in each primary image. Then, as an aggregate, the method provides the ability to calculate the 2D area and the 3D volume of the structure or organ, fluid filled or non-fluid filled, from the summation of each 2D image.

The method employs subjecting each primary image to a pre-filtering step using nonlinear filters to enhance the image. The pre-filtering step includes an image-smoothing step to obtain maximum contrast between organ wall boundaries followed by an image-sharpening step to establish image enhancements. The pre-filtering step has a first algorithm and a second algorithm, each algorithm having a partial differential equation (PDE) formula in non-linear form. The first PDE algorithm serves as a heat filter, and the second PDE algorithm serves as a shock filter. The sequence of image enhancement is application of the heat filter followed by application of the shock filter. Each image is subjected to a combination of the heat and shock filters to reduce each image's signal noise and to sharpen each image signal while at the same time preserving signal discontinuities. Each primary image subjected to the heat and shock prefiltering algorithms is formed into a second image having a clearer demarcation along the boundary of the structure or organ walls.

Each second image is then processed to determine where to locate initial edge points by either of two locating methods. A first locating method is a manual, user-deployed radial point method. The radial point method is comprised of lines that are drawn in substantially 30-degree increments for establishing where maximum spatial gradients exist during transitioning between light and dark areas. A second locating method to set initial boundary edge points is an automatic method to determine the leading and trailing regions of wall locations along an A-mode first dimension (1D) scan line that is regulated by a hysteresis threshold value.

An optimal pathway to connect between the initial edge points is then determined using a third algorithm to determine an optimal pathway. The optimal pathway between any two points is one defined to have the least cost, where the least cost represents the sum of three sub-equations; namely, the edge distance cost, the path direction cost, and the previous contour distance cost. The optimal pathway represents an automatically implemented way to draw contour boundary lines along wall structure using the automatically selected initial edge points from the second locating method or as manually selected by the radial method. The advantages compared to the manual live wire methodology is fewer initial points are needed to establish boundary contours, the minimum cost-optimal pathway algorithm is more robust, and does not require manual, interactive mouse pointer setting and reselecting.

After the boundaries of each structure or organ are determined in each second image, the 2D area and 3D volume of the organ or structure is determined. For fluid-filled organs, this includes but is not limited to bladders, amniotic sacs, prostates, cardiac chambers (left and right ventricles, left and right atriums), ovarian cysts, arteries, and veins. Similarly, non-fluid containing organs or structures includes but is not limited to kidneys, kidney stones, gall bladders, gall bladder stones, and ovaries.

Finally, the method may be done remotely using a web server to analyze scan data sent from ultrasound, CT, MR, and PET devices over intranets or internets where the device architecture permits image processing on the server-side of the invention.

DETAILED DESCRIPTION OF THE PREFERRED EMBODIMENT

Figure 1:
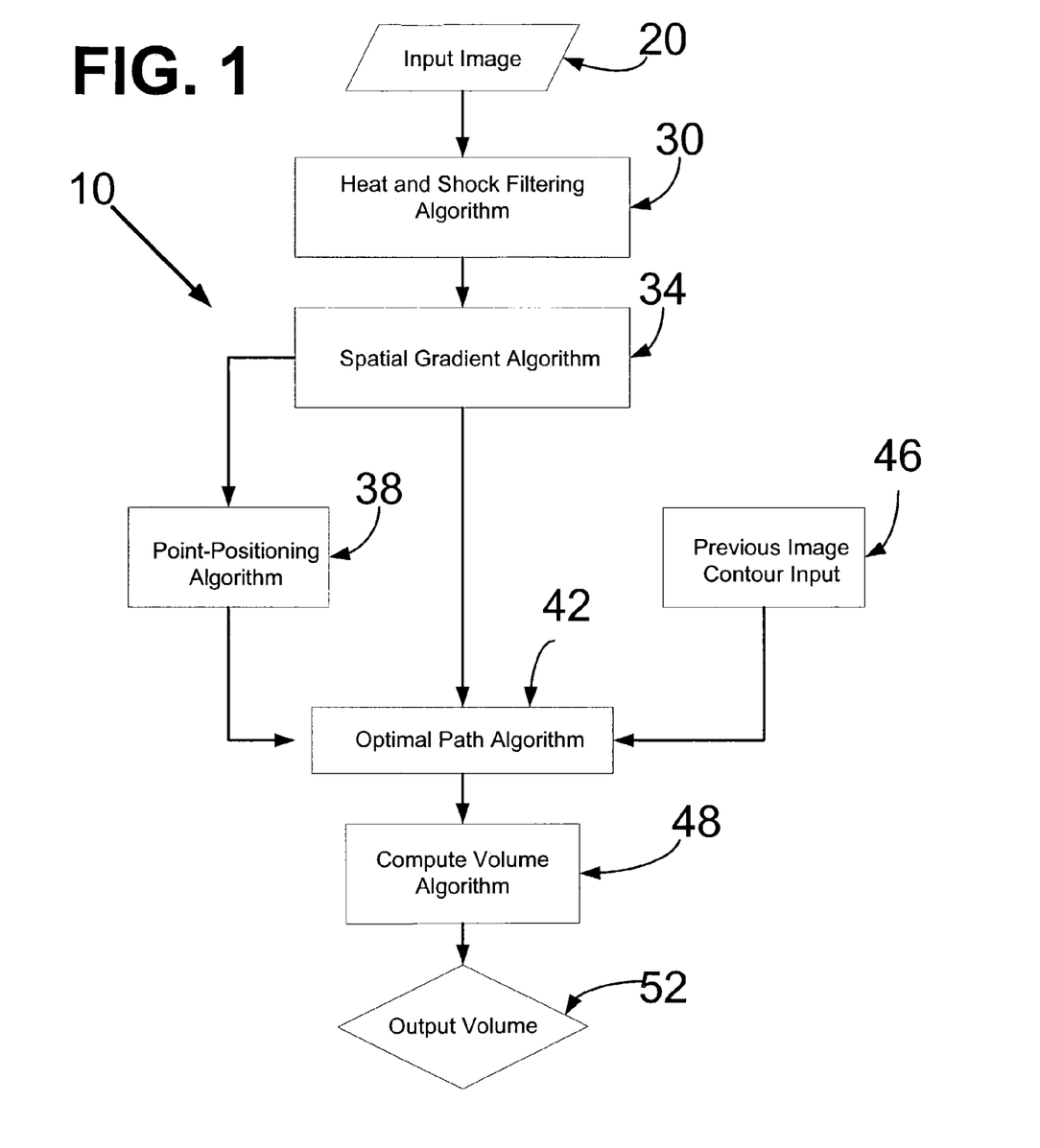
FIG. 1 is an overview of the segmentation algorithm method.

FIG. 1 shows an overview of a segmentation algorithm 10. The segmentation algorithm 10 begins with the receiving of an input image 20, to which a heat and shock filtering algorithm 30 is applied to the input image 20. Thereafter, a spatial gradient algorithm 34 is applied to the image that has been heat and shock filtered. At this juncture, initial edge points are located in a point-positioning algorithm 38 to the boundary of the organ structure within the image. Thereafter an optimal path algorithm 42 is applied to determine the best path to connect the initial edge points assigned by the point-positioning algorithm 38. This optimal path algorithm 42 also uses the result of the spatial gradient algorithm 34 as an input. For images already having a drawn contour, a previous image contour input 46 is inputted to the optimal path algorithm 42. Thereafter, a compute volume algorithm 48 is applied to the image, and the computed volume is reported as an output volume 52.

Figure 2:
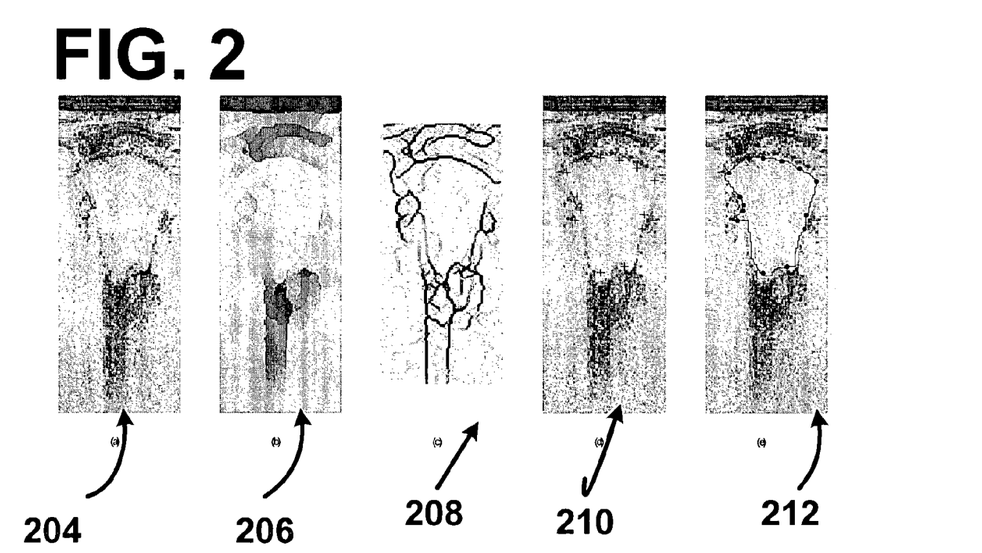
FIG. 2 is an algorithm processing on a real bladder image presented in a five-panel series.

FIG. 2 shows the segmentation algorithm applied to a sample image. An original bladder image 204 acquires more contrast as shown in a bladder image 206 once subjected to the heat and shock filtering algorithms. Thereafter, spatial gradients are depicted as shown in a bladder image 208. Initial points are placed as shown in a bladder image 210 when the point-positioning algorithm is applied. The point-positioning algorithm includes the radial method. Finally, a contour along the boundary where the points have been connected by applying the optimal path algorithm is shown in a bladder image 212.

Figures 3A, 3B:
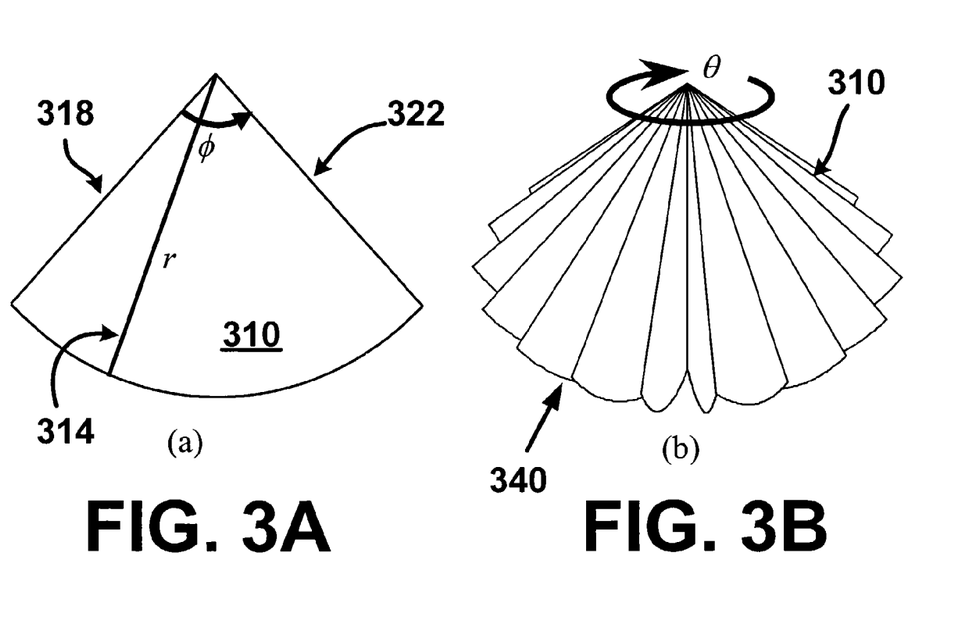
FIG. 3A is a depiction of a 1D scans line forming a 2D scan plane.
FIG. 3B is a depiction of a plurality of scan planes forming a 3D image cone.

FIG. 3A depicts the 1D and 2D operational aspects of a single element transducer that rotates mechanically about an angle Φ. A scanline 314 of length r migrates between a first limiting position 318 and a second limiting position 322 as determined by the value of the angle Φ, creating a fan-like 2D scan plane 310. In the image shown in FIG. 2, the x-axis is the tilt angle ϕ, and the y-axis is the scanline depth r. The single element transducer operates substantially at 3.7 MHz frequency and creates an approximately 18 cm deep scan line 314 and migrates within the angle Φ having an angle value substantially near 0.07 radians. A first motor tilts the transducer 600 clockwise and then counterclockwise forming a 120° sector image.

The 3D ultrasound data is depicted in FIG. 3B that shows the scanplane 310 among a plurality of scanplanes substantially assembled into a rotational array. After gathering a 2D sector image, a second motor rotates the transducer 15° to gather the next 120° sector image. This process is repeated until the transducer is rotated through 180°, resulting in a cone-shaped 3D image 340 data set with 12 planes. The 3D image 340 is a rotational array of assembled scanplanes. The tilt angle ϕ, indicates how much the scanline is tilted from the center line in 2D sector image, and the rotation angle θ, identifies which rotation plane the sector image lies in. Therefore, any point in this 3D data set can be isolated using plane coordinates expressed as three parameters, P(r,ϕ,θ). The rotational scanplane array as depicted by 3D image 340 in FIG. 3B represents one preferred embodiment. Other preferred embodiment includes scanplanes arrays assembled from wedge scans and substantially rectangular translational scans. Yet other preferred embodiments include images formed by line arrays, either spiral distributed or reconstructed random-lines. The line arrays are defined using points identified by the coordinates expressed by the three parameters, P(r,Φ,θ), where the values or r, ϕ, and θ can vary.

Figure 4:
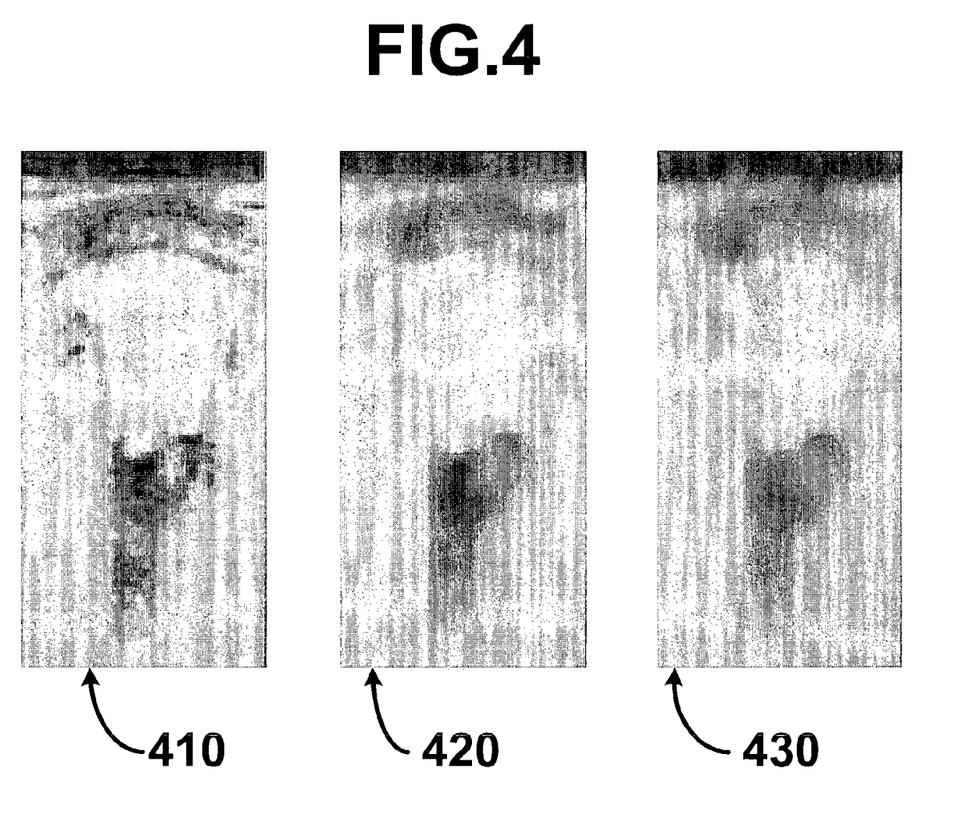
FIG. 4 is a three panel series of 2D images smoothed with varying heat filter algorithm iterations.

The effects of applying the heat filtering algorithm is shown in FIG. 4. The effect of 10 iterations of heat algorithm is shown in image 410. The effect of 50 iterations is shown in image 420. The effect of 100 iterations is shown in image 430. With more iterations of heat filtering algorithms, the more the image becomes blurry.

For scanplanes substantially equivalent to scanplane 310, the algorithms are expressed in two-dimensional terms and use formulas to convert scanplane pixels (picture elements) into area units. For the scan cones substantially equivalent to the 3D conic array 340, the algorithms are expressed in three-dimensional terms and use formulas to convert voxels (volume elements) into volume units. The heat-filtering algorithm is determined one of the simplest PDE for image processing is the heat equation as shown in equation E1:

$$\frac{\partial u}{\partial t} = \frac{\partial^2 u}{\partial x^2} + \frac{\partial^2 u}{\partial y^2}, \qquad \text{E1}$$

where u is the image being processed whose initial value is the input image: $u_0 = I$.

The above PDE can be discretized using finite differences to give the following iterative scheme of equation E2:

$$\frac{u_{i,j}^{t+1} - u_{i,j}^{t}}{k} = (u_{i+1,j}^{t} - 2u_{i,j}^{t} + u_{i-1,j}^{t}) + (u_{i,j+1}^{t} - 2u_{i,j}^{t} + u_{i,j-1}^{t}) \qquad \text{E2}$$

which can be simplified as shown in equation E3:

$$u_{i,j}^{t+1} = u_{i,j}^{t} + k(u_{i+1,j}^{t} + u_{i-1,j}^{t} + u_{i,j+1}^{t} + u_{i,j-1}^{t} - 4u_{i,j}^{t}) \qquad \text{E3}$$

where k is the time step, and $u_{i,j}^{t}$ is the value of the pixel at coordinates (i,j) at time point (iteration) t.

This heat equation results in a smoothing of the image substantially equivalent to the Gaussian filtering of the image. The larger the number of iterations the more the input image is smoothed or blurred.

Shock filters are another type of PDE-based filters that were originally proposed by Osher and Rudin (Osher and Rudin 1990) for sharpening of signals and images: A one-dimensional shock filter is given as equation E4:

$$\frac{\partial u}{\partial t} = -\text{sign}\left(\frac{\partial^2 u}{dx^2}\right)\left|\frac{\partial u}{dx}\right| \qquad \text{E4}$$

where u is the image being processed, $$\frac{\partial^2 u}{\partial x^2}$$

is the second partial derivative of u, $$\left|\frac{\partial u}{dx}\right|$$

is the absolute value of the first derivative of u along the x-axis. Here, the signal is modified based on the sign of its second derivative and the magnitude of its first derivative. This filter cannot be discretized using the simple centered finite-difference scheme.

Figure 5A:
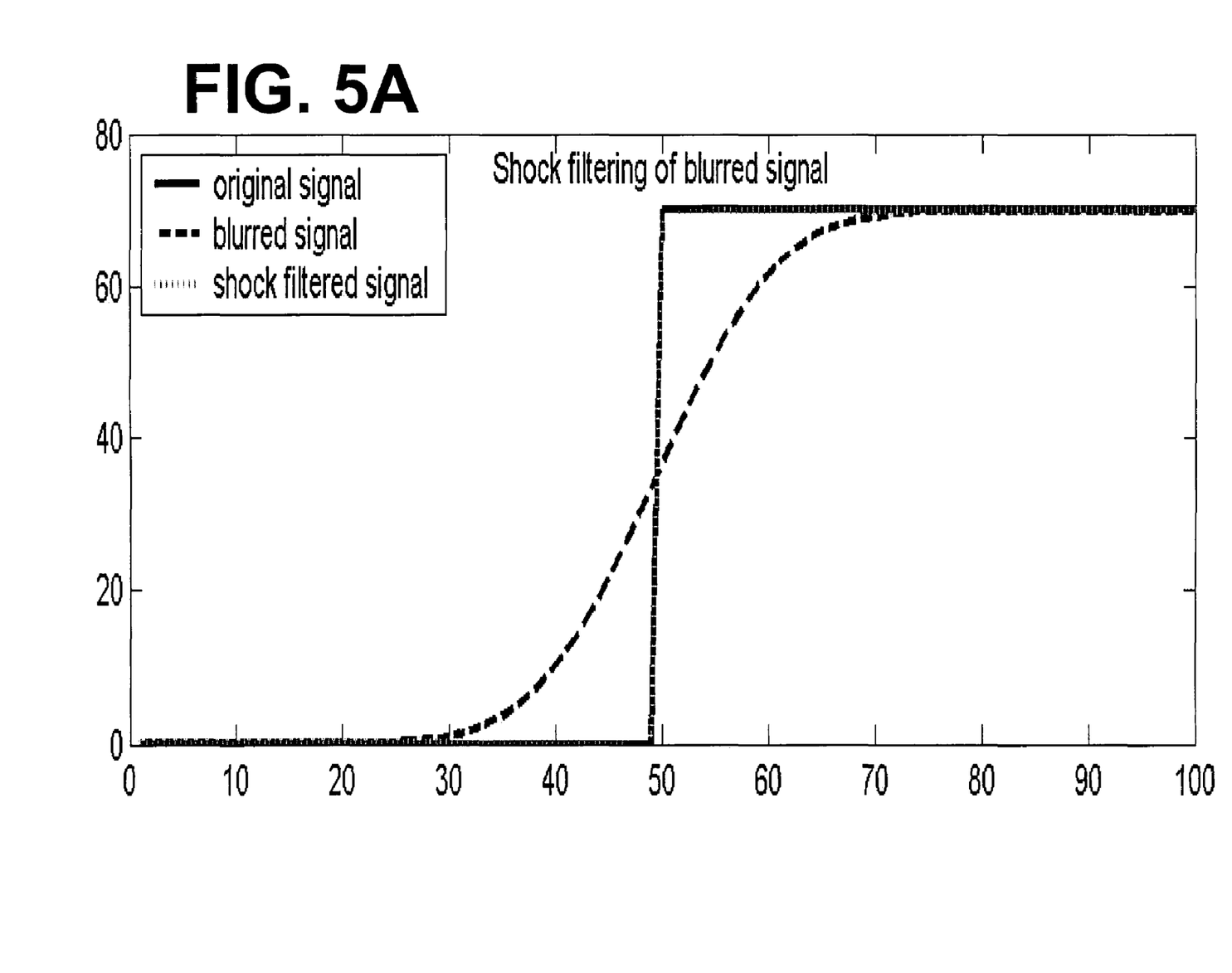
FIG. 5A is a graph showing the effects of a shock-filtering algorithm of a blurred signal.

The result of applying this filter on noiseless blurred data is shown in FIG. 5A. The x-axis shows the index coordinates of the signals while the y-axis shows the magnitude of the signals. The solid line is the original noiseless signal which was blurred with a Gaussian filter algorithm. The blurred signal is shown as the dotted line. A shock filter was then applied to the blurred signal and that results in the signal shown in light shaded line—it is virtually the same as the original signal and the edge is restored from the blurred signal.

Figure 5B:
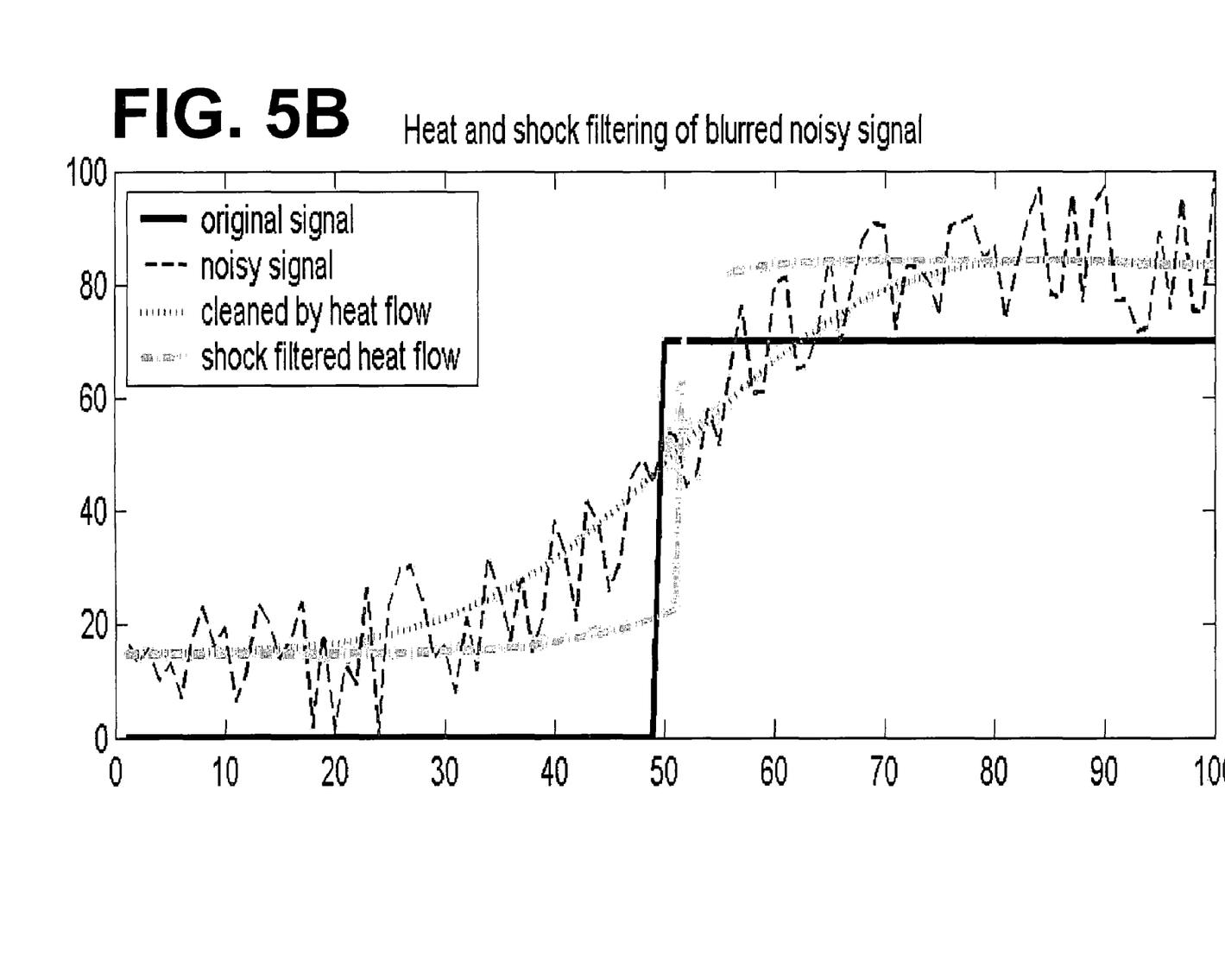
FIG. 5B is a graph showing the effects of heat and shock filtering algorithms of a blurred noisy signal.

Applying this filter directly to noisy data, however, does not work and leads to many possible false edges. The combination of heat and shock filters would works very well at reducing noise and sharpening of a signal while preserving the significant discontinuities on a signal. First, the noisy signal is filtered using the 1D heat filter (Equation E1), which results in the reduction of noise and smoothing of edges. This step is followed by a shock-filtering step (Equation E4), which results in the sharpening of the blurred signal. A 1D simulated example of this combination heat/shock filter is shown in FIG. 5B. The solid line is the original noiseless signal while the dotted dark line is the noisy blurred signal. The result of heat filtering the noisy signal by the gray dashed line. Finally, the result of shock filtering after heat filtering is shown by the gray dot-dashed line. Note that on the last signal, the significant edge has been preserved while the noise has been removed.

In two dimensions, the shock filter PDE specified by Osher and Rudin is:

$$\frac{\partial u}{\partial t} = -F(l(u))\|\nabla u\|,$$ E5 where $\lambda(u)$ is the Laplacian of the image (u, F.) is a function of the Laplacian, and $\|\nabla u\|$ is the gradient magnitude. For the Laplacian, the second derivative in the direction of the gradient is used:

$$\lambda(u) = u_{xx}u_x^2 + 2u_{xy}u_x u_y + u_{yy}u_y^2$$ E6

For the function F, to avoid placing spurious edges at points with small gradient values as would occur by choosing the sign by selecting the sign of the Laplacian in the 1-D case, the following function is used instead:

$$F(l(u)) = 1, \text{ if } l(u) > 0 \text{ and } \|\nabla u\| > t$$
$$= -1, \text{ if } l(u) < 0 \text{ and } \|\nabla u\| > t$$
$$= 0, \text{ otherwise}$$

where t is a threshold on gradient values.

Once again, as in the 1D case, a combination of the heat and shock filters works very well at reducing noise and sharpening of a signal while preserving the significant edges on an image. FIG. 2—image 208 shows the results of applying the heat and shock filter on real ultrasound data.

The point-positioning algorithm uses two different methods for locating the initial edge points. One method looks for edges along radial lines and the other looks for edges along A-mode lines. The first method requires the user to specify a center point from which radial lines are drawn for an image, and the second method is completely automatic. In the first method, to locate the initial edge points on an image, the image is radially sampled from the user marked center location. The radial lines are drawn at substantially in 30-degree increments. On each radial line, edge points are found by using the values obtained from the spatial gradient algorithm. A first point on each radial line whose gradient magnitude exceeds a pre-set threshold and which represents a transition from a dark area to a bright area. If no such point is found, that radial line is skipped. As shown in FIG. 2 image 210, the points are assigned to the edge locations.

In the second method, the A-mode lines starting from the transducer position are moved outwards. One-dimensional gradients and pixel intensity values I are used along these A-mode lines to determine fluid wall locations. A hysteresis threshold is applied to the gradient values to determine the leading wall and the trailing wall of the structure.

Given two points on an image, p1 and p2, an optimal path finding algorithm finds the "best" path between the two points where "best" is the one that has the least cost. The cost function for a path can be defined to depend upon many factors such as, how close the path passes through edges on an image, the direction of the path, how smooth the path is, and what the length of the path is. A dynamic programming algorithm can be then used to locate the least cost path between p1 and p2.

The total cost function to be a weighted is defined by a sum of 3 terms:

$$C(p) = \alpha C_e(p) + \beta C_d(p) + \gamma C_c(p)$$ E7 where $\alpha$, $\beta$, and $\gamma$ are numerical values and the three cost terms are:

1. Edge Distance Cost $C_e(p)$: This cost is defined such that paths closer to high gradient points, i.e., edges, are favored over other paths.

$$C_e(p) = \sum_{i=p1}^{p2} \left(\frac{1}{\mu + \|\nabla I_i\|}\right),$$ E8 where $I_i$ is the pixel intensity at point i, $\|\nabla I_i\|$ is the gradient magnitude of point i, and $\mu$ is a small constant. Since this term is the sum of inverse image gradients for each pixel on the path—this cost term implicitly favors shorter paths over longer paths.

Figure 6:
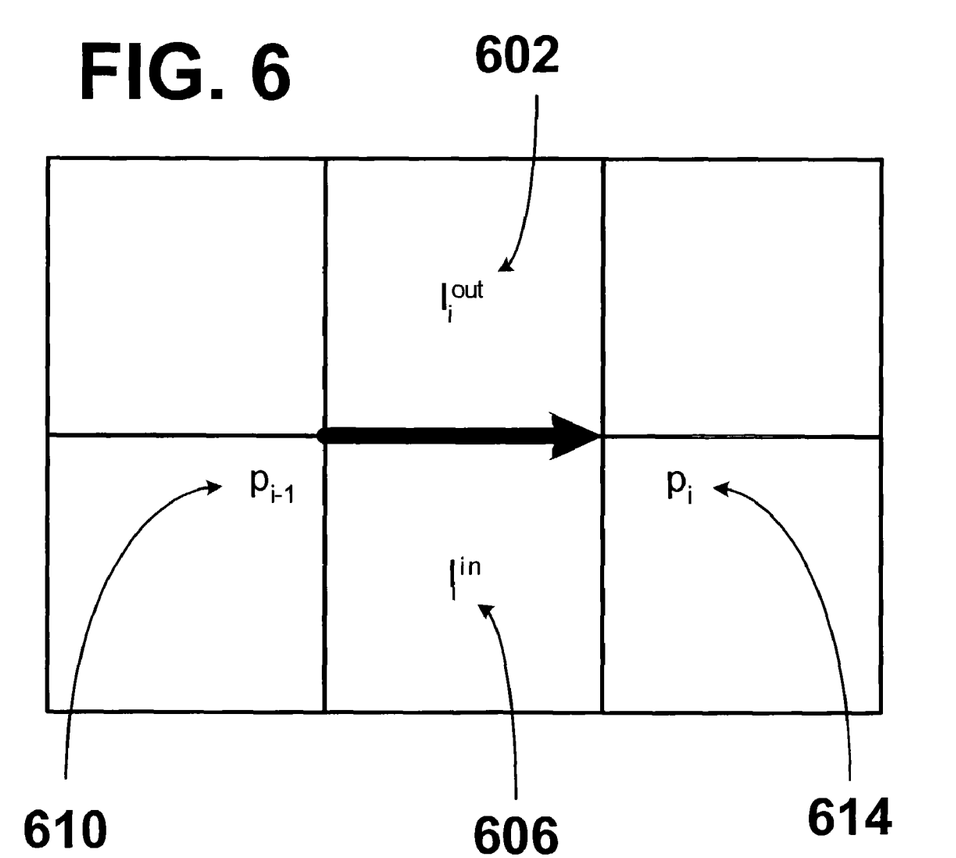
FIG. 6 is a pixel-processing algorithm for finding the direction cost.

2. Path Direction Cost: Since the path between $p^1$ and $p^2$ is a directed graph, a cost can be defined based on the orientation of the graph. The cost is defined to favor paths for which pixels on the inside of the path are dark and the pixels on the outside are bright (See FIG. 6). The PDE formula for calculating the path direction cost is provided in equation E9.

$$C_d(p) = \sum_{i=p1}^{p2} (I_i^{in} - I_i^{out}),$$ E9 where $I_i^{in}$ and $I_i^{out}$ are the image intensities on the inside and the outside of the path connecting point i and $i_{-1}$ as shown in FIG. 6. FIG. 6 depicts, at the pixel level, how the optimal path algorithm is applied. Direction of path proceeds from point 610 ($p_{i-1}$) to point 614 ($p_i$) between the outside pixel 602 ($I_i^{out}$) and the inside pixel 606 ($I_i^{in}$). Given two points on the image, $p_{i-1}$ 610 and $p_i$ 614, an optimal path finding algorithm finds the "best" path between the two points where "best" is the one that has the least cost and bisects the. Thus $I_i^{in}$ pixel 606 is the image intensity of the inside and dark pixel and $I_i^{out}$ 610 is the image intensity outside and bright pixel along a path bisecting the $I_i^{in}$ 606 and $I_i^{out}$ 602 pixels and connecting pixels points i 614 and $i_{-1}$ 610 adjacent to each side of the $I_i^{in}$ 606 pixel.

3. Previous Contour Distance Cost: When trying to find paths in 3D images, a constraint upon the paths on the current image are imposed and are close to a contour on a previous image. Therefore, a definition of a cost based on the distance of a point on the current path to a contour from a previous image can be made as according to equation E 10:

$$C_c(p) = \sum_{i=p1}^{p2} D_i^P \qquad \text{E 10}$$

where P is the previous contour and $D_i^P$ is the distance of point i from the closest point on the previous contour. This distance can be easily evaluated using the Euclidean distance transform function computed for the previous contour.

A dynamic programming algorithm was used to find the least cost path between the initial edge points. The two steps typically involved in this are: (1) Computing the cost of the path from the starting point to each point on the image—this cost image (also known as the minimum action surface) using the fast-marching algorithms; (2) Locating the path connecting the end point to the starting point by gradient descent on the minimum action surface.

This multi-step segmentation algorithm of the present invention serves to establish a determination of the best path between two points and makes the segmentation much more robust. When the two points are quite far apart on the image, it still locates a good path that passes through the significant edges and completing the areas with missing edges.

FIG. 2 image 212 shows the optimal path found using this algorithm connecting the initial edge points.

The first image processed was the central image that had the fewest missing lateral boundaries. No previous contour constraint was used for this central image.

From this central image; the process was moved up to process all the images after the central image through the end of the sequence and then moved down to process all the images before the central image through the beginning of the sequence.

After the contours on all the images have been delineated, the volume of the segmented structure is computed. The contour inside the polygon is filled using a polygon filling algorithm to compute the volume. Then, the intensity value of a central pixel is determined using trilinear interpolation (where intensity values from six three-dimensional neighbors are used) to create a Cartesian volume from the polar coordinate images. Pixels on the boundary are assigned fractional values depending on the partial volume coverage. Finally, the sum of all the pixels in the reconstructed volume is multiplied by the voxel resolution to get the volume.

The segmentation algorithm was made on images from a bladder phantom and on images of the bladder from several subjects. Boundaries were delineated on all of the images in the 3D dataset using the same center point for all images in the 3D sequence.

Figure 7:
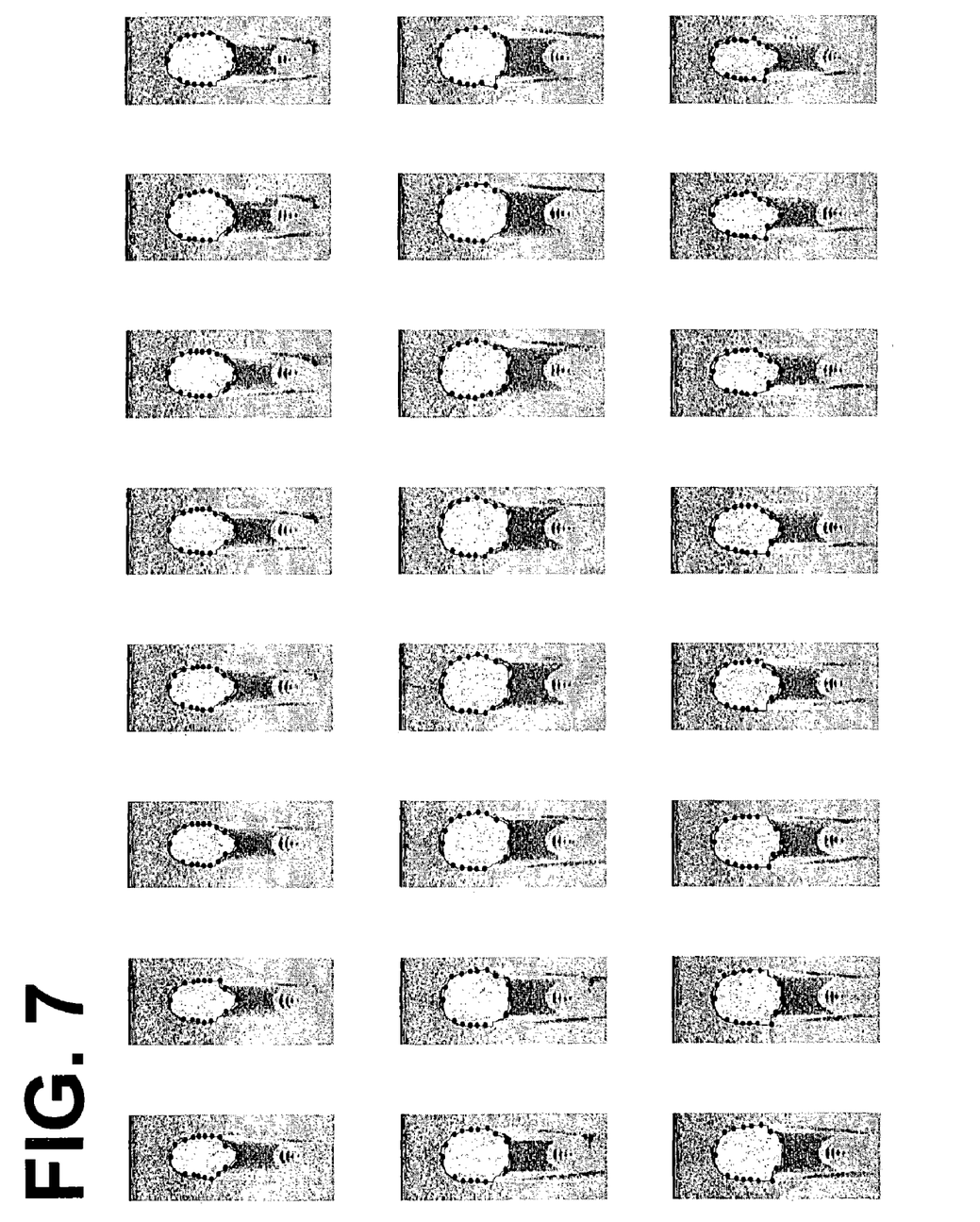
FIG. 7 is a 24 panel series of segmentation algorithms applied to 24 image planes of a bladder phantom, each image plane showing the resultant boundary contours.

The segmentation algorithm was first tested on a bladder phantom with a known volume. From the bladder phantom 24 planes of data are acquired. The boundaries detected on this phantom are shown in FIG. 7.

While the true volume of the bladder phantom is known to be 495 mL, the volume computed using our algorithm is 483 mL, or 97.6% accurate.

The accuracy for clinical measurements fared well. The segmentation algorithms as applied to 12 scan planes of real bladder images from five different subjects (3 females and 2 males) are shown in Table 1. The volume of urine was measured using a UroFlow device. The segmentation algorithm of the present invention was applied to images to measure volumes and compared to the urine volumes measured by the UroFlow device. The volume measured by the Uroflow device added to the post-Uroflow volume is considered the true bladder as a standard to compare to the volume determined by the segmentation algorithms applied to the 12 bladder scan images from each patient.

The table below shows the raw results on the five subjects:

TABLE 1

Bladder volume computational results

| Subject ID | True Bladder Volume (mL) | Segmentation Algorithm (mL) | Accuracy (%) |
| --- | --- | --- | --- |
| 102 | 391 | 367 | 93.9% |
| 130 | 238 | 232 | 97.5% |
| 138 | 651 | 642 | 98.6% |
| 148 | 469 | 434 | 92.5% |
| 162 | 169 | 104 | 61.5% |

Accuracy is defined as a % ratio and is calculated by taking the volume determined from the Segmentation Algorithm applied to the 12 image scans and dividing it by the True Bladder Volume, then multiplied by 100. The accuracy range of the 12 scan plane measurements to measured urine volumes is 61.5% to 98.6%. The median is 93.9%. The mean accuracy for the five measurements is 88.8%.

Figure 8:
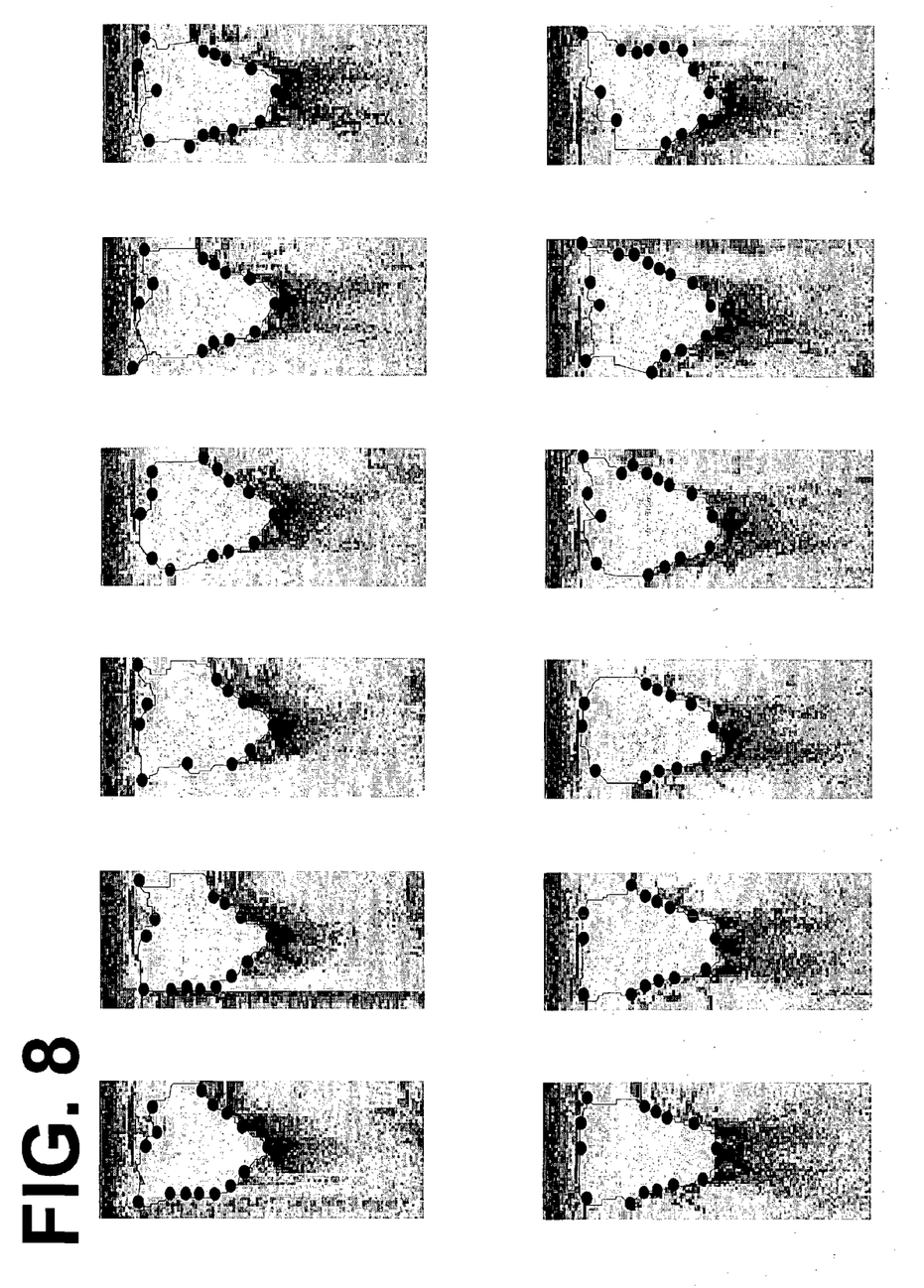
FIG. 8 is a 12 panel series of segmentation algorithms applied to a first human bladder scanned with 12 images planes, each image plane showing the resultant boundary contours.
Figure 9:
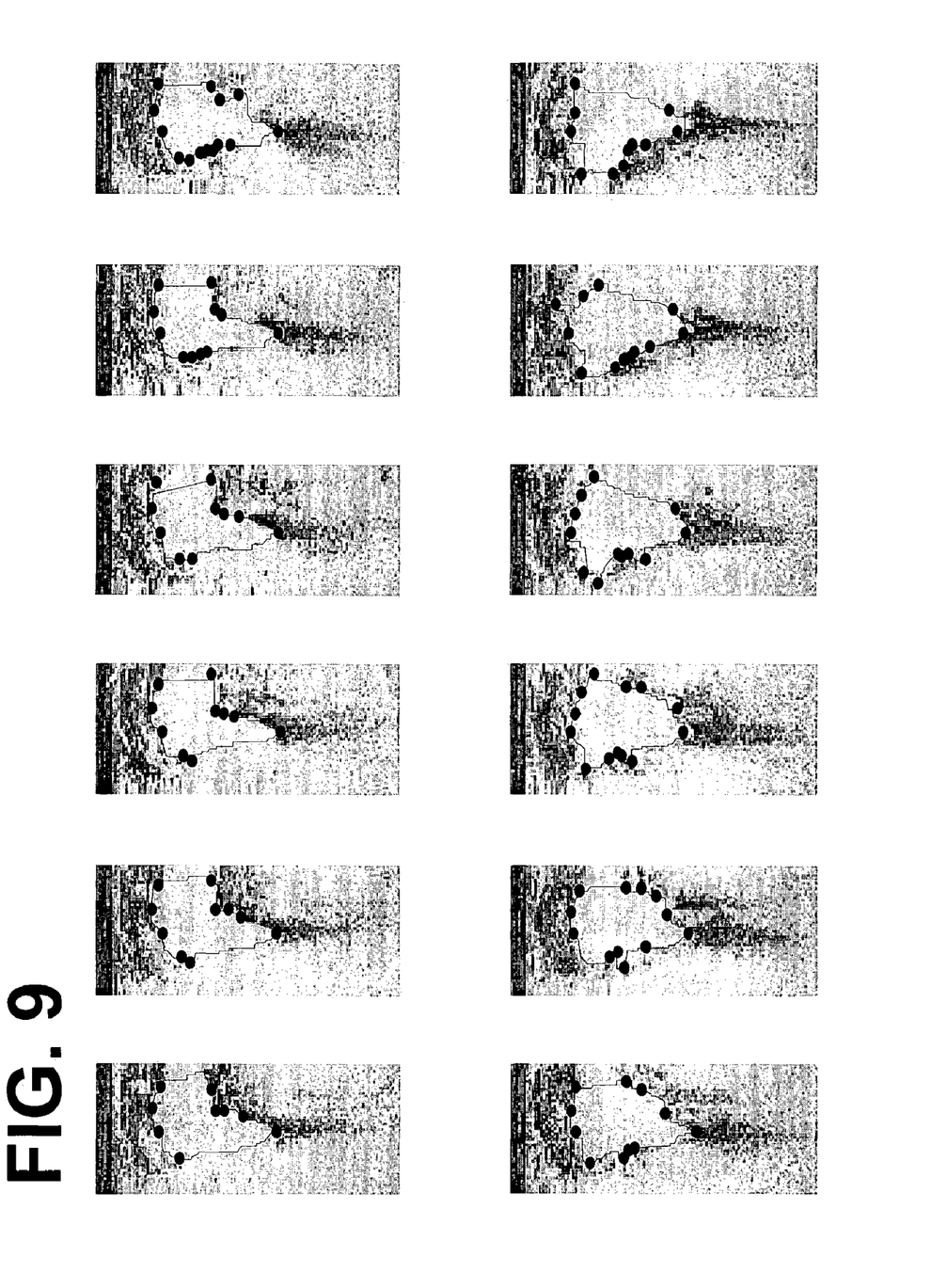
FIG. 9 is a 12 panel series of segmentation algorithms applied to a second human bladder scanned with 12 image planes, each image plane showing the resultant boundary contours.

FIG. 8 and FIG. 9 respectively show the delineated bladder boundaries of 12 scan plane images for patients 138 and 148 subjected to the segmentation algorithm of the present invention. The segmentation algorithm set boundaries very reasonable boundaries except at a few planes in that the initial edge point is outside the expected location.

The segmentation algorithm of the present invention involves fitting minimum cost contours to known boundary points. The cost function is defined very similarly to snakes and other deformable models; however, instead of modifying an initial contour, our algorithm finds an optimal path between two known points on the boundary. The advantages compared to deformable models are: (a) The initial set of points needs to be very small and you do not need an entire initial contour, (b) The algorithm is more robust with respect to missing boundaries since missing boundaries are simply handled through an least cost path through them, (c) The algorithm is not iterative and always finds a unique global minimum for the cost function.

While the preferred embodiment of the invention has been illustrated and described, as noted above, many changes can be made without departing from the spirit and scope of the invention. For example, other uses of the invention include determining the areas and volumes of the prostate, heart, and other organs and body regions of clinical interest. Accordingly, the scope of the invention is not limited by the disclosure of the preferred embodiments.

We claim:

1. A method for determining areas of structures from an image, the method comprising:

acquiring a digital image;

enhancing the digital image using non-linear filters;

segmenting the digital image using a spatial gradient algorithm, a initial point positioning algorithm, and an optimal path algorithm that combines the spatial gradient and the initial point positioning algorithms to produce homogeneous regions; and determining the areas of the homogenous regions.

2. The method of claim 1, wherein the non-linear filters include a heat filter and a shock filter, the heat filter applied to the digital image followed by application of the shock filter to the digital image.

3. The method of claim 2, wherein the heat filter is defined by a partial differential equation of an inputted image pixel intensity u expressed in an equation defined as $$\frac{\partial u}{\partial t} = \frac{\partial^2 u}{\partial x^2} + \frac{\partial^2 u}{\partial y^2},$$

where u is the image being processed, $$\frac{\partial^2 u}{\partial x^2}$$

is the second partial derivative of u along the x-axis, and $$\frac{\partial^2 u}{\partial y^2}$$

is the second partial derivative of u along the y-axis.

4. The method of claim 2, wherein the shock filter is a partial differential equation of an imputed image pixel intensity u expressed in an equation defined as $$\frac{\partial u}{\partial t} = -\text{sign}\left(\frac{\partial^2 u}{dx^2}\right)\left|\frac{\partial u}{dx}\right|,$$

where u is the image being processed, $$\frac{\partial^2 u}{\partial x^2}$$

is the second partial derivative of u, $$\left|\frac{\partial u}{dx}\right|$$

is the absolute value of the first derivative of u along the x-axis.

5. The method of claim 1, wherein the optimum path algorithm includes a total cost function C(p) weighted between an edge distance cost function, a path direction cost function, and a previous contour distance cost function from the equation $$C(p) = \alpha C_e(p) + \beta C_d(p) + \gamma C_c(p),$$

where $C_e(p)$ is the edge distance cost function, $C_d(p)$ is the path direction cost function, $C_c(p)$ is the previous contour distance cost function, and $\alpha$, $\beta$, and $\gamma$ are numerical values.

6. The method of claim 5, wherein the edge distance function $C_e(p)$ is defined from the equation $$C_e(p) = \sum_{i=p1}^{p2}\left(\frac{1}{\mu + \|\nabla I_i\|}\right),$$

where $I_i$ is the pixel intensity, $\|\nabla I_i\|$ is the gradient magnitude the pixel at location i, and $\mu$ is a constant value.

7. The method of claim 5, wherein the path direction cost function $C_d(p)$ is defined from the equation $$C_d(p) = \sum_{i=p1}^{p2}(I_i^{in} - I_i^{out}),$$

where $I_i^{in}$ is the image intensity of the inside and dark pixel and $I_i^{out}$ is the image intensities the outside and bright pixel along a path bisecting the $I_i^{in}$ and $I_i^{out}$ pixels and connecting pixels points i and $i_{-1}$ adjacent to each side of the $I_i^{in}$ pixel.

8. The method of claim 5, wherein the previous contour function $C_c(p)$ is defined by the equation $$C_c(p) = \sum_{i=p1}^{p2} D_i^P,$$

where P is the previous contour and $D_i^P$ is the distance of point i from the closest point on the previous contour.

9. A method for determining volumes of structures from a set of images, the method comprising:
acquiring at least two digital images;
enhancing each digital image using non-linear filters;
segmenting the digital image using a spatial gradient algorithm, a initial point positioning algorithm, and an optimal path algorithm that combines the spatial gradient and the initial point positioning algorithmto produce homogeneous regions;
assembling the digital images into an array;
determining the areas of and the volumes between the homogeneous regions in the array.

10. The method of claim 9, wherein the array includes a rotational assembly, a wedge assembly, and a translational assembly.

11. The method of claim 9, wherein the non-linear filters include a heat filter and a shock filter, the heat filter applied to the digital image followed by application of the shock filter to the digital image.

12. The method of claim 11, wherein the heat filter is defined by a partial differential equation of an inputted image pixel intensity u expressed in an equation defined as:

$$\frac{\partial u}{\partial t} = \frac{\partial^2 u}{\partial x^2} + \frac{\partial^2 u}{\partial y^2},$$

where u is the image being processed, $$\frac{\partial^2 u}{\partial x^2}$$

is the second partial derivative of u along the y-axis.

13. The method of claim 11, wherein the shock filter is a partial differential equation of an imputed image pixel intensity u expressed in an equation defined as $$\frac{\partial u}{\partial t} = -\text{sign}\left(\frac{\partial^2 u}{dx^2}\right)\left|\frac{\partial u}{dx}\right|,$$

where u is the image being processed, $$\frac{\partial^2 u}{\partial x^2}$$

is the second partial derivative of u, $$\left|\frac{\partial u}{dx}\right|$$

is the absolute value of the first derivative of u along the x-axis.

14. The method of claim 9, wherein the optimum path algorithm includes a total cost function C(p) weighted between an edge distance cost function, a path direction cost function, and a previous contour distance cost function from the equation $$C(p) = \alpha C_e(p) + \beta C_d(p) + \gamma C_c(p),$$

where $C_e(p)$ is the edge distance cost function, $C_d(p)$ is the path direction cost function, $C_c(p)$ is the previous contour distance cost function, and α, β, and γ are numerical values.

15. The method of claim 14, wherein the edge distance function $C_e(p)$ is defined from the equation $$C_e(p) = \sum_{i=p1}^{p2} \left(\frac{1}{\mu + \|\nabla I_i\|}\right),$$

where $I_i$ is the pixel intensity, $\|\nabla I_i\|$ is the gradient magnitude the pixel at location i, and μ is a constant value.

16. The method of claim 14, wherein the path direction cost function $C_d(p)$ is defined from the equation $$C_d(p) = \sum_{i=p1}^{p2} (I_i^{in} - I_i^{out}),$$

where $I_i^{in}$ is the image intensity of the inside and dark pixel and $I_i^{out}$ is the image intensities the outside and bright pixel along a path bisecting the $I_i^{in}$ and $I_i^{out}$ pixels and connecting pixels points i and $i_{-1}$ adjacent to each side of the $I_i^{in}$ pixel.

17. The method of claim 14, wherein the previous contour function $C_c(p)$ is defined by the equation $$C_c(p) = \sum_{i=p1}^{p2} D_i^P,$$

where P is the previous contour and $D_i^P$ is the distance of point i from the closest point on the previous contour.

18. A method to determine volume of a structure in digital images acquired from electromagnetic and non-electromagnetic sources, the method comprising:
positioning a transceiver exterior to a patient such that at least a portion of the structure is within a field of view of the transceiver, the transceiver, configured to send electromagnetic radiation and to receive echoes of the electromagnetic radiation;
sending the radiation from the transceiver to the structure;
receiving echoes of the radiation reflected from the structure to the transceiver;
associating the received echoes to form a plurality of 2D scanplanes so that they form an array;
enhancing the images of the structure in each plane of the array using non-linear filters; and
determining the structure volume spanning between and through each plane in the array.

19. The method of claim 18, wherein plurality of 2D scanplanes are assembled into a plurality of arrays including a rotational array, a translational array, or a wedge array.

20. The method of claim 18, wherein the non-linear filters include a heat filter and a shock filter, the heat filter applied to the digital images followed by application of the shock filter to the digital images.

21. The method of claim 20, wherein the heat filter is defined by a partial differential equation of an inputted image pixel intensity u expressed in an equation defined as $$\frac{\partial u}{\partial t} = \frac{\partial^2 u}{\partial x^2} + \frac{\partial^2 u}{\partial y^2},$$

where u is the image being processed, $$\frac{\partial^2 u}{\partial x^2}$$

is the second partial derivative of u along the x-axis, and $$\frac{\partial^2 u}{\partial y^2}$$

is the second partial derivative of u along the y-axis.

22. The method of claim 20, wherein the shock filter is a partial differential equation of an imputed image pixel intensity u expressed in an equation defined as $$\frac{\partial u}{\partial t} = -\text{sign}\left(\frac{\partial^2 u}{dx^2}\right)\left|\frac{\partial u}{dx}\right|,$$

where u is the image being processed, $$\frac{\partial^2 u}{\partial x^2}$$

is the second partial derivative of u, $$\left|\frac{\partial u}{dx}\right|$$

is the absolute value of the first derivative of u along the x-axis.

23. The method of claim 18, wherein the plurality algorithms includes a spatial gradient algorithm, a previous contour algorithm, and. an optimal path algorithm that combines the spatial gradient and the previous contour algorithms to produce the homogeneous regions.

24. The method of claim 23, wherein the optimum path algorithm includes a total cost function C(p) weighted between an edge distance cost function, a path direction cost function, and a previous contour distance cost function from the equation $$C(p) = \alpha C_e(p) + \beta C_d(p) + \gamma C_c(p),$$

where $C_e(p)$ is the edge distance cost function, $C_d(p)$ is the path direction cost function, $C_c(p)$ is the previous contour distance cost function, and $\alpha$, $\beta$, and $\gamma$ are numerical values.

25. The method of claim 24, wherein the edge distance function $C_e(p)$ is defined from the equation $$C_e(p) = \sum_{i=p1}^{p2} \left(\frac{1}{\mu + \|\nabla I_i\|}\right),$$

where $I_i$ is the pixel intensity, $\|\nabla I_i\|$ is the gradient magnitude the pixel at location i, and $\mu$ isconstant value.

26. The method of claim 24, wherein the path direction cost function $C_d(p)$ is defined from the equation $$C_d(p) = \sum_{i=p1}^{p2} (I_i^{in} - I_i^{out}),$$

where $I_i^{in}$ is the image intensity of the inside and dark pixel and $I_i^{out}$ is the image intensities the outside and bright pixel along a path bisecting the $I_i^{in}$ and $I_i^{out}$ pixels and connecting pixels points i and $i_{-1}$ adjacent to each side of the $I_i^{in}$ pixel.

27. The method of claim 24 wherein the previous contour function $C_c(p)$ is defined by the equation.

$$C_c(p) = \sum_{i=p1}^{p2} D_i^P,$$

where P is the previous contour and $D_i^P$ is the distance of point i from the closest point on the previous contour.

\* \* \* \* \*